(12) United States Patent
Smith

(10) Patent No.: US 8,954,158 B2
(45) Date of Patent: Feb. 10, 2015

(54) MULTI-ELECTRODE CHANNEL CONFIGURATIONS

(75) Inventor: Zachary M. Smith, Englewood, CO (US)

(73) Assignee: Cochlear Limited, Macquarie University, NSW (AU)

( * ) Notice: Subject to any disclaimer, the term of this patent is extended or adjusted under 35 U.S.C. 154(b) by 503 days.

(21) Appl. No.: 12/366,510

(22) Filed: Feb. 5, 2009

(65) Prior Publication Data

US 2010/0198301 A1 Aug. 5, 2010

(51) Int. Cl.
*A61N 1/36* (2006.01)
*A61N 1/05* (2006.01)

(52) U.S. Cl.
CPC .......... *A61N 1/0541* (2013.01); *A61N 1/36032* (2013.01)
USPC ............................................................ 607/57

(58) Field of Classification Search
USPC .................................................... 607/55–57
See application file for complete search history.

(56) References Cited

U.S. PATENT DOCUMENTS

| | | | |
|---|---|---|---|
| 4,532,930 | A | 8/1985 | Crosby et al. |
| 4,648,403 | A | 3/1987 | Van Compernolle |
| 5,793,875 | A | 8/1998 | Lehr et al. |
| 6,249,704 | B1 | 6/2001 | Maltan et al. |
| 6,537,200 | B2 | 3/2003 | Leysieffer et al. |
| 6,565,503 | B2 | 5/2003 | Leysieffer et al. |
| 6,575,894 | B2 | 6/2003 | Leysieffer et al. |
| 6,594,525 | B1 | 7/2003 | Zierhofer |
| 6,594,526 | B2 | 7/2003 | Betzold |
| 6,697,674 | B2 | 2/2004 | Leysieffer |

(Continued)

FOREIGN PATENT DOCUMENTS

| | | |
|---|---|---|
| WO | 01/13991 | 3/2001 |
| WO | 0113991 A1 | 3/2001 |

(Continued)

OTHER PUBLICATIONS

Boex et al. "Electrical field interactions in different cochlear implant systems" J. Acoust. Soc. Am. vol. 114, Issue 4, pp. 2049-2057 (Oct. 2003).

(Continued)

*Primary Examiner* — Eric D. Bertram

(57) ABSTRACT

An apparatus and method optimizing complex channel configurations to produce minimal channel interactions is provided. The method includes selecting multiple channels from a channel configuration including a plurality of channels, each of the plurality of channels includes multiple electrodes. The method also includes measuring an interaction between selected channels and determining a significance of the measured interaction. The method further includes adjusting a focus of the channel configuration based on the significance of measured interaction, wherein the focus of the channel configuration is not adjusted if the interaction between the selected channels determined to be insignificant. The measuring, determining and adjusting is repeated until the interaction between the selected channels is determined to be insignificant or the magnitude of the interaction is determined to be minimized, thereby optimizing the channel configuration for the selected channels. Another set of channels from the channel configuration is selected and the measuring, determining, adjusting and repeating is performed for each set until full channel configuration is optimized.

24 Claims, 9 Drawing Sheets

(56) References Cited

U.S. PATENT DOCUMENTS

| | | | |
|---|---|---|---|
| 6,754,356 | B1 | 6/2004 | Luo et al. |
| 6,778,858 | B1 | 8/2004 | Peeters |
| 7,110,821 | B1 * | 9/2006 | Ross .............................. 607/57 |
| 7,184,843 | B1 | 2/2007 | Cohen |
| 7,426,414 | B1 | 9/2008 | Litvak et al. |
| 7,860,573 | B2 | 12/2010 | van den Honert |
| 2003/0105504 | A1 | 6/2003 | Zierhofer |
| 2005/0187592 | A1 | 8/2005 | Seligman et al. |
| 2005/0192648 | A1 | 9/2005 | Killian et al. |
| 2006/0247735 | A1 | 11/2006 | Honert |
| 2007/0135862 | A1 | 6/2007 | Nicolai et al. |
| 2009/0024185 | A1 | 1/2009 | Kulkarni |
| 2011/0093038 | A1 | 4/2011 | Honert |
| 2011/0288613 | A1 | 11/2011 | Smith et al. |

FOREIGN PATENT DOCUMENTS

| | | |
|---|---|---|
| WO | 2006119069 | 11/2006 |
| WO | 2010091177 | 8/2010 |

OTHER PUBLICATIONS

Clopton et al., "Electrode Configuration and Spread of Neural Excitation: Compartmental Models of Spiral Ganglion Cells," Clark & Cowan, International Cochlear Implant, Speech and Hearing Symposium, 1995 Ann. Otol. Rhinol. Laryngol. Suppl. 166, pp. 115-118.
Eddington et al. "Auditory Prostheses Research With Multiple Channel Intracochlear Stimulation in Man". Ann Otol Rhinol Laryngol.; Nov.-Dec. 1978;87(6 Pt 2):5-39.
European Search Report for 06751841 dated Nov. 9, 2009.
Favre et al. "Channel interactions in patients using the Ineraid multichannel cochlear implant." Hearing Research. Apr. 1993;66(2):150-6.
International Search Report for PCT/US2006/016353 dated May 17, 2007.
International Search Report for PCT/US2010/023191, dated Mar. 31, 2010.
Jolly et al., "Quadrupolar Stimulation for Cochlear Prostheses: Modeling and Experimental Data," IEEE Trans. Biomd. Eng., vol. 43, No. 8, pp. 857-865, Aug. 1996.
Kral et al., "Spatial Resolution of Cochlear Implants: The Electrical Field and Excitation of Auditory Afferents," Hearing Research 121, pp. 11-28, 1998.
Miyoshi et al., "Proposal of a New Auditory Nerve Stimulation Method for Cochlear Prosthesis," Artificial Organs, 20 (8): pp. 941-946, 1996.
Norgia et al., "Measurement of Electrode Current Pulses from Cochlear Implants". Proceedings of the 21st IEEE. Como, Italy: IEEE May 18-20, 2004, vol. 3, p. 1697-1700.
Rodenhiser et al. "A Solution to the Inverse Problem: A Method for Determining the Driving Currents for Focused Stimulation". Oct. 31, 1991. New Frontiers of Biomedical Engineering Innovations From Nuclear to Space Technology 13th Annual International Conference of the IEEE Engineering in Medicine and Biology Society: Oct. 31-Nov. 3, 1991, Orlando, Florida, ISA: Proceeding, XP010102083.

Rodenhiser et al., "A Method for Determining the Driving Currents for Focused Stimulation in the Cochlea," IEEE Trans. Biomd. Eng. 42(4), pp. 337-342, Apr. 1995.
Shannon, Robert V. "Multichannel electrical stimulation of the auditory nerve in man. I. Basic psychophysics." Hearing Research Aug. 1983;11(2):157-89.
Suesserman et al. "Lumped-parameter model for in vivo cochlear stimulation" IEEE Transactions on Biomedical Engineering. vol. 40, Issue: 3. Publication Date: Mar. 1993. pp. 237-245.
Townshend et al., "Pitch Perception by Cochlear Implant Subjects," J. Coust. Soc. Am., 82(1): 106-115, 1987.
Townshend et al., "Reduction of Electrical Interaction in Auditory Prostheses," IEEE Tran. Biomd. Eng., BME-34, No. 11, pp. 891-897, 1987.
Van Compernolle, Dirk, "A Computational Model of the Cochlea used with Cochlear Prosthesis Patients," in: Acoustics, Speech, and Signal Processing, IEEE International Conference on ICASSP '85, vol. 10, pp. 427-429, 1985.
Van Compernolle, Dirk, "Speech Processing Strategies for a Multichannel Cochlear Prosthesis," Ph. D. Dissertation, Stanford University, 1985.
van den Honert et al. "Focused intracochlear electric stimulation with phased array channels" Journal of Acoustic Society America 121(6) Jun. 2007, pp. 3703-3716.
Vanpoucke et al. "Identification of the impedance model of an implanted cochlear prosthesis from intracochlear potential measurements" IEEE Transactions on Biomedical Engineering. Publication Date: Dec. 2004 vol. 51, Issue: 12. pp. 2174-2183.
White et al. "Multichannel Cochlear Implants" Archives of Otolaryngol. 1984;110(8):493-501.
White et al., "Current Spreading and Speech-Processing Strategies for Cochlear Prostheses," Clark & Busby, International Cochlear Implant Symposium, Ann. Otol. Rhino. Laryng. 96 (Suppl. 128), pp. 22-24, 1987.
Written Opinion for PCT/US2010/023191, dated Mar. 31, 2010.
Extended European Search Report for European Application No. 10739119.5 mailed Feb. 26, 2013 (9 pages).
International Search Report for International Application No. PCT/IB2011/052170 mailed Sep. 22, 2011 (5 pages).
International Preliminary Report on Patentability for International Application No. PCT/IB2011/052170 mailed Nov. 29, 2012 (11 pages).
Bonham B H et al., "Current focusing and steering: Modeling, physiology, and psychophysics", Hearing Research, Elsevier Science Publishers, Amsterdam, NL, vol. 242, No. 1-2, Aug. 1, 2008, pp. 141-153.
Office Action for Australian Application No. 2006242390 mailed Nov. 17, 2010 (3 pages).
Office Action for Chinese Application No. 200680023866.8 mailed Jan. 8, 2010 with English Translation (4 pages).
Office Action for Chinese Application No. 200680023866.8 mailed Sep. 21, 2011 with English Translation (14 pages).
Office Action for Japanese Application No. 2008-509192 mailed Jan. 25, 2011 with English Translation (4 pages).

* cited by examiner

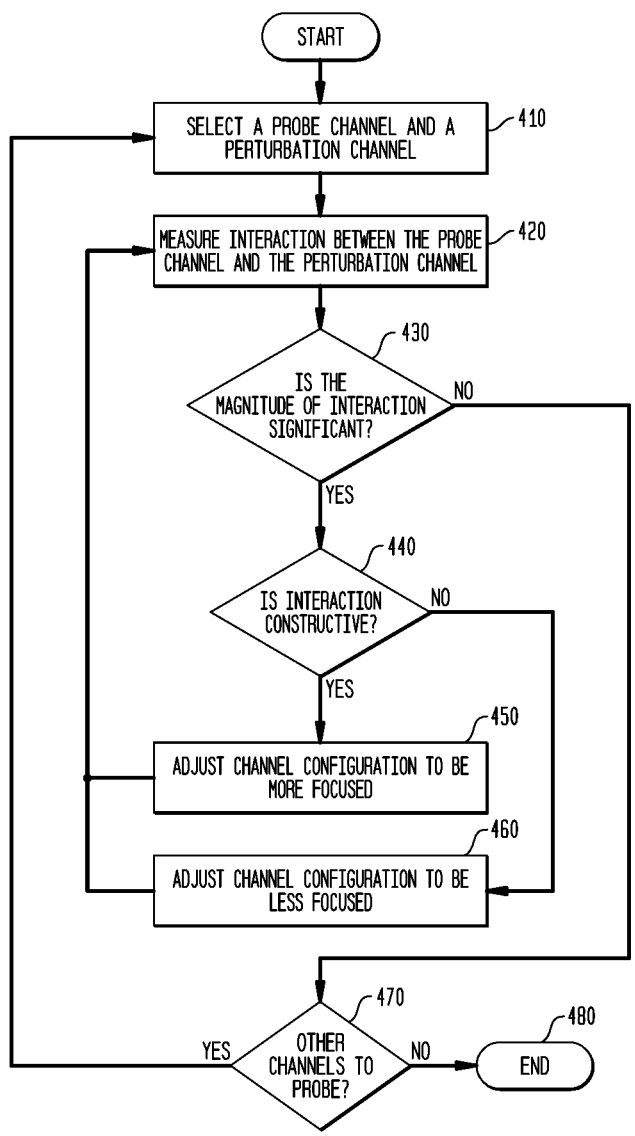

SAME POLARITY

OPPOSITE POLARITY

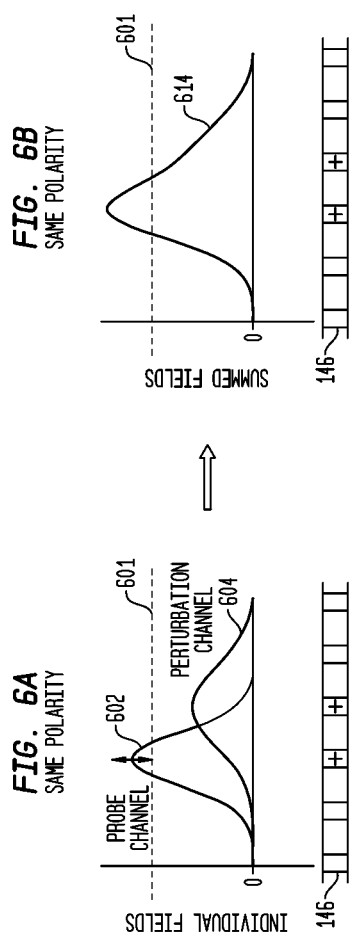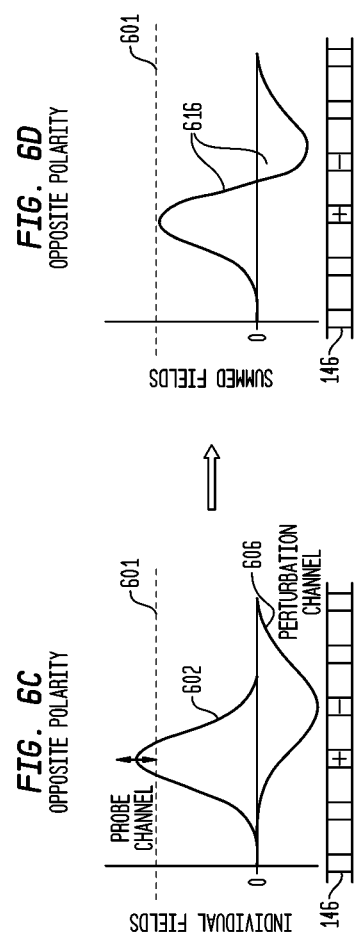

MULTI-ELECTRODE CHANNEL CONFIGURATIONS

BACKGROUND

1. Field of the Invention

The present invention relates to a stimulating medical device, and more particularly, to using multi-electrode channel configurations in a stimulating medical device.

2. Description of the Related Art

To compensate for a deficiency, such as a loss of hearing, several electrical stimulation devices use electrical signals to activate nerve or muscle fibers in a recipient. In particular, a prosthetic hearing device or implant works by directly stimulating functioning auditory nerves inside the cochlea with electric fields stimulated through electric current pulses. These implant devices typically include a microphone that receives incoming sound and a signal processor that converts selected portions of the incoming sounds into corresponding stimulating signals based on a selected speech strategy. An internal receiver implanted beneath the skin receives the signals and delivers electric current pulses to an array of electrodes coiled inside the cochlea. The electrodes stimulate the auditory nerve fibers in the cochlea and the resulting electrical sound information is carried along the auditory nerve to the brain for interpretation. Each electrode may provide monopolar or bipolar stimulation. Monopolar stimulation is stimulation delivered from a single intracochlear electrode to a remote extracochlear electrode. Bipolar stimulation occurs when stimulation flows from nearby, paired intracochlear electrodes. Bipolar stimulation focuses the stimulation more and presumably stimulates a smaller, more localized population of auditory nerve fibers. Monopolar stimulation, on the other hand, spreads current over a wider area and stimulates a larger population of neurons.

Using monopolar stimulation, current implant devices cannot focus stimulation on target neurons that are electrically distant from the stimulating electrodes. For example, in implant devices which use electrodes placed along the length of the scala tympani to stimulate the spiral ganglion cells, there is an inability to focally stimulate small subpopulations of spiral ganglion cells with monopolar stimulation of the placed electrodes. Because the bone surrounding the scalae has relatively higher impedance than the fluid perilymph and tissues that fill the scalae, stimulation currents tend to spread longitudinally along the length of the cochlea. Longitudinal current spread results in relatively broad neural excitation patterns compared to those elicited by narrowband acoustic stimulation in healthy ears. Attempts to narrow the broad neural excitation patterns caused by monopolar stimulation have been made using channel configurations with two or more nearby electrodes to source and sink all or some of the current. But, when multiple channels are stimulated simultaneously with the same polarity, electric fields add up and neural stimulation patterns combine in a non-linear fashion. While channel configurations of multiple electrodes may result in more focused patterns, there is still usually some significant channel interactions between nearby channels. To avoid the negative impact of channel interactions, which tend to be greatest with monopolar channel configurations, most current implant devices use stimulation strategies that incorporate sequential or temporally "interleaved" stimulation patterns.

SUMMARY

In one aspect of the invention there is provided a method for adjusting weights of a stimulating device comprising a plurality of stimulation channels, wherein each stimulation channel comprises a plurality of electrodes each having a corresponding weight. This method comprises: selecting a probe channel from amongst the plurality of stimulation channels, selecting at least one perturbation channel from amongst the plurality of stimulation channels; applying stimulation via the probe channel using the plurality of electrodes and their corresponding weights; applying stimulation via at least one perturbation channel, and adjusting one or more weights for at least one of the stimulation channels based on an interaction between the stimulation from the probe channel and the one or more perturbation channels.

In another aspect there is provided an apparatus for use in adjusting weights of a stimulating device comprising a plurality of stimulation channels. This apparatus comprises: a selector configured to select a probe channel from amongst the plurality of stimulation channels, wherein the probe channel comprises a plurality of electrodes each associated with a corresponding weight, and to select at least one perturbation channel from amongst the plurality of stimulation channels; a stimulation controller configured to transmit information for applying stimulation via the probe channel using the plurality of electrodes and their corresponding weights, and stimulation via at least one perturbation channel; and a weight adjuster configured to adjust one or more weights for at least one of the stimulation channels based on an interaction between the stimulation from the probe channel and the stimulation from the one or more perturbation channels.

In yet another aspect there is provided a computer program embodied on a computer readable medium, the computer program comprising program code for controlling a processor to execute a method for adjusting weights of a stimulating device comprising a plurality of stimulation channels, wherein each stimulation channel comprises a plurality of electrodes each having a corresponding weight. This method comprises selecting a probe channel from amongst the plurality of stimulation channels, selecting at least one perturbation channel from amongst the plurality of stimulation channels, applying stimulation via the probe channel using the plurality of electrodes and their corresponding weights; applying stimulation via at least one perturbation channel; and adjusting one or more weights for at least one of the stimulation channels based on an interaction between the stimulation from the probe channel and the one or more perturbation channels.

In yet another aspect there is provided an apparatus for adjusting weights of a stimulating device comprising a plurality of stimulation channels, wherein each stimulation channel comprises a plurality of electrodes each having a corresponding weight. This apparatus comprises: means for selecting a probe channel from amongst the plurality of stimulation channels; means for selecting at least one perturbation channel from amongst the plurality of stimulation channels; means for applying stimulation via the probe channel using the plurality of electrodes and their corresponding weights; means for applying stimulation via at least one perturbation channel; and means for adjusting one or more weights for at least one of the stimulation channels based on an interaction between the stimulation from the probe channel and the one or more perturbation channels.

BRIEF DESCRIPTION OF THE DRAWING

Embodiments of the present invention are described below with reference to the attached drawings, in which:

FIG. 4 is a high-level flow chart illustrating operations that may be performed for adjusting complex stimulation channel weights, in accordance with an embodiment.

FIG. 6A illustrates a probe channel electric field and a perturbation channel electric field where the perturbation channel has the same polarity as the probe channel;

FIG. 6B illustrates the combined electric field resulting from the combined the probe channel electric field and perturbation channel electric field where the polarities are the same.

FIG. 6C illustrates the probe channel electric field and a perturbation channel electric field where the perturbation channel has the opposite polarity as the probe channel.

FIG. 6D illustrates the combined electric field resulting from the combined the probe channel electric field and perturbation channel electric field 606 where the polarities are opposite;

DETAILED DESCRIPTION

Aspects of the present invention are generally directed to determining stimulation channels for a stimulating device. In an embodiment, an initial set of stimulation channels are determined in which each stimulation channel provides stimulation using a plurality of weighted electrodes. An iterative process is then employed that minimizes the interactions of the stimulation channels by adjusting the electrode weights for the stimulation channels. This iterative process may employ selecting one of the stimulation channels as a probe channel and a neighboring channel as a perturbation channel. The probe and perturbation channels are then stimulated and the interaction between the two channels is measured. If the measured interaction exceeds a threshold, the weights are adjusted and stimulation is again applied on the probe and perturbation channels using the new weights. This process is then repeated until the measured channel interaction falls below the threshold. Another set of stimulation channels may then be selected as the probe channel and the perturbation channel, and the process repeated until the measured channel interactions for all stimulation channels as the probe channels are found to be below the threshold. These weights may then be used by the stimulating device for applying stimulation via the stimulation channels.

Embodiments of the present invention are described herein primarily in connection with one type of hearing prosthesis, namely a Cochlear™ prostheses (commonly referred to as Cochlear™ prosthetic devices, Cochlear™ implants, Cochlear™ devices, and the like; simply "cochlear implants" herein.) Cochlear implants generally refer to hearing prostheses that deliver electrical stimulation to the cochlea of a recipient. As used herein, cochlear implants also include hearing prostheses that deliver electrical stimulation in combination with other types of stimulation, such as acoustic or mechanical stimulation. It would be appreciated that embodiments of the present invention may be implemented in any cochlear implant or other hearing prosthesis now known or later developed, including auditory brain stimulators, or implantable hearing prostheses that acoustically or mechanically stimulate components of the recipient's middle or inner ear.

Figure 1:
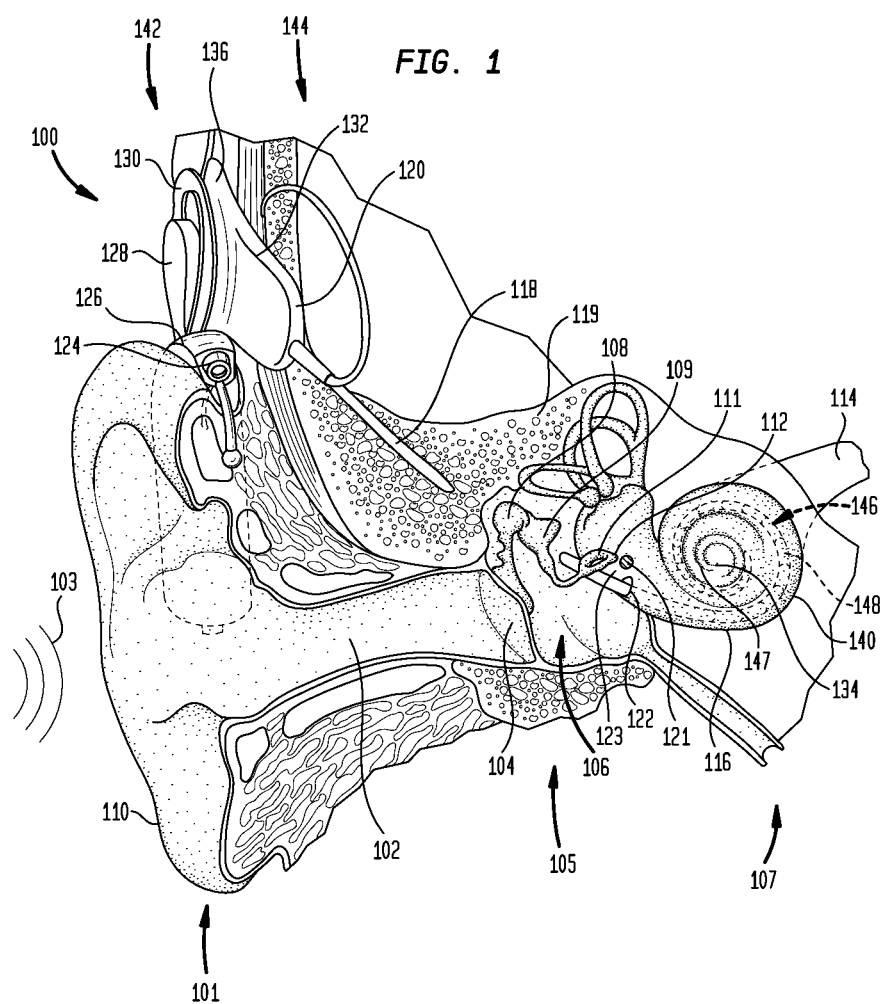
FIG. 1 is perspective view of a cochlear implant, in which embodiments of the invention may be implemented.

FIG. 1 is a perspective view of a conventional cochlear implant, referred to as cochlear implant 100 implanted in a recipient having an outer ear 101, a middle ear 105 and an inner ear 107. Components of outer ear 101, middle ear 105 and inner ear 107 are described below, followed by a description of cochlear implant 100.

In a fully functional ear, outer ear 101 comprises an auricle 110 and an ear canal 102. An acoustic pressure or sound wave 103 is collected by auricle 110 and channeled into and through ear canal 102. Disposed across the distal end of ear canal 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109 and the stapes 111. Bones 108, 109 and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

Cochlear implant 100 comprises an external component 142 which is directly or indirectly attached to the body of the recipient, and an internal component 144 which is temporarily or permanently implanted in the recipient. External component 142 typically comprises one or more sound input elements, such as microphone 124 for detecting sound, a sound processing unit 126, a power source (not shown), and an external transmitter unit 128. External transmitter unit 128 comprises an external coil 130 and, preferably, a magnet (not shown) secured directly or indirectly to external coil 130. Sound processing unit 126 processes the output of microphone 124 that is positioned, in the depicted embodiment, by auricle 110 of the recipient. Sound processing unit 126 generates encoded signals, sometimes referred to herein as encoded data signals, which are provided to external transmitter unit 128 via a cable (not shown).

Internal component 144 comprises an internal receiver unit 132, a stimulator unit 120, and an elongate electrode assembly 118. Internal receiver unit 132 comprises an internal coil 136, and preferably, a magnet (also not shown) fixed relative to the internal coil. Internal receiver unit 132 and stimulator unit 120 are hermetically sealed within a biocompatible housing, sometimes collectively referred to as a stimulator/receiver unit. The internal coil receives power and stimulation data from external coil 130, as noted above. Elongate electrode assembly 118 has a proximal end connected to stimulator unit 120, and a distal end implanted in cochlea 140. Electrode assembly 118 extends from stimulator unit 120 to cochlea 140 through mastoid bone 119, and is implanted into cochlea 104. In some embodiments electrode assembly 118 may be implanted at least in basal region 116, and sometimes further. For example, electrode assembly 118 may extend towards apical end of cochlea 140, referred to as cochlear apex 134. In certain circumstances, electrode assembly 118 may be inserted into cochlea 140 via a cochleostomy 122. In other circumstances, a cochleostomy may be formed through round window 121, oval window 112, the promontory 123 or through an apical turn 147 of cochlea 140.

Electrode assembly 118 comprises a longitudinally aligned and distally extending array 146 of electrodes 148, sometimes referred to as electrode array 146 herein, disposed along a length thereof. Although electrode array 146 may be disposed on electrode assembly 118, in most practical applications, electrode array 146 is integrated into electrode assembly 118. As such, electrode array 146 is referred to herein as being disposed in electrode assembly 118. Stimulator unit 120 generates stimulation signals which are applied by electrodes 148 to cochlea 140, thereby stimulating auditory nerve 114.

In cochlear implant 100, external coil 130 transmits electrical signals (i.e., power and stimulation data) to internal coil 136 via a radio frequency (RF) link. Internal coil 136 is typically a wire antenna coil comprised of multiple turns of electrically insulated single-strand or multi-strand platinum or gold wire. The electrical insulation of internal coil 136 is provided by a flexible silicone molding (not shown). In use, implantable receiver unit 132 may be positioned in a recess of the temporal bone adjacent auricle 110 of the recipient.

Because the cochlea is tonotopically mapped, that is, partitioned into regions each responsive to stimulus signals in a particular frequency range, frequencies may be allocated to one or more electrodes of the electrode assembly to generate an electric field in positions in the cochlea that are close to the region that would naturally be stimulated in normal hearing. This enables the prosthetic hearing implant to bypass the hair cells in the cochlea to directly deliver electrical stimulation to auditory nerve fibers, thereby allowing the brain to perceive hearing sensations resembling natural hearing sensations. In achieving this, processing channels of the sound processing unit 126, that is, specific frequency bands with their associated signal processing paths, are mapped to a set of one or more electrodes to stimulate a desired nerve fiber or nerve region of the cochlea. Such sets of one or more electrodes for use in stimulation are referred to herein as "electrode channels" or "stimulation channels."

Figure 2:
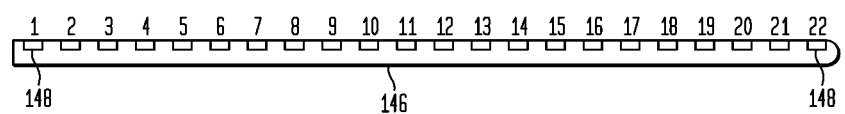
FIG. 2 illustrates a more detailed view of an electrode array, in accordance with an embodiment.

FIG. 2 illustrates a more detailed view of an electrode array 146 comprising a plurality of electrodes 148, in accordance with an embodiment. Electrode array 146 may be used to apply different modes of stimulation, such as, for example, monopolar, bipolar, tripolar, or phased-array stimulation. The below discussed embodiments will generally be discussed with reference to a cochlear implant system in which the electrode array 146 provides complex stimulation channels. As used herein, a complex stimulation channel refers to a stimulation channel that uses three or more electrodes 148, such as, for example, a tripolar stimulation channel or a phased-array stimulation channel. In a tripolar stimulation channel (also referred to as quadrupolar stimulation), current flows from a center electrode (e.g., electrode 3) and returns to each of two neighboring electrodes (e.g., electrodes 2 and 4)s. Tripolar stimulation may also be used with an extra-cochlea electrode in which the extra-cochlea electrode (not shown) partially sinks the current flowing from the center electrode (e.g., electrode 3) in conjunction with the two neighboring electrodes (e.g., electrodes 2 and 4). As will be discussed in further detail below, each of these sink electrodes (e.g., electrodes 2 and 4 and the extra-cochlea electrode) may be weighted so that the each sink electrode sinks a percentage of the current flowing from the center electrode (e.g., electrode 3) in accordance with the electrode's assigned weight.

In phased-array stimulation, weights are assigned to a plurality of electrodes (e.g., electrodes 1-5, 2-8, all electrodes, etc.) and the stimulation is applied using the weighted electrodes. Phased-array stimulation may also be used in conjunction with a weighted extra-cochlea electrode (not shown). Phased-array stimulation is discussed in more detail in U.S. patent application Ser. No. 11/414,360 by Chris van den Honert, entitled "Focused Stimulation in a Medical Stimulation Device" and Chris van den Honert and David C. Kelsall, "Focused Intracochlear Electric Stimulation with Phase Array Channels," J. Acoust. Soc. Am., 121, 3703-3716 (June 2007), both of which are incorporated by reference herein in the entirety. These references are hereinafter collectively referred to as "the van den Honert references."

Figure 3:
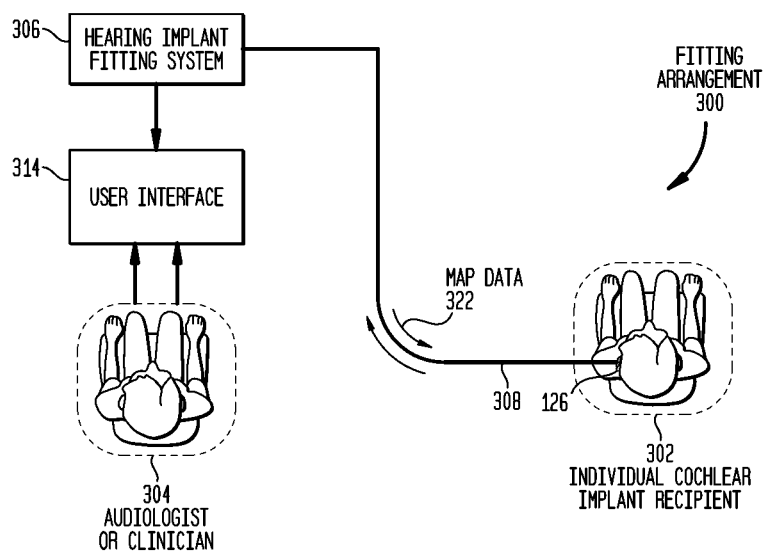
FIG. 3 is a schematic diagram illustrating one exemplary arrangement in which a hearing implant fitting system may be used to assign and adjust complex stimulation channel electrode weights, in accordance with an embodiment.

FIG. 3 is a schematic diagram illustrating one exemplary arrangement 300 in which a hearing implant fitting system 306 may be used to assign and adjust complex stimulation channel electrode weights, in accordance with an embodiment. As shown in FIG. 3, an audiologist or clinician 304 may use a hearing implant fitting system 306 ("fitting system" herein) comprising interactive software and computer hardware to create individualized recipient map data 322 that are digitally stored on system 306 and ultimately downloaded to the memory of the sound processing unit 126 for recipient 302. System 306 may be programmed and/or implement software programmed to carry out one or more of the functions of mapping, neural response measuring, acoustic stimulating, and recording of neural response measurements and other stimuli.

In the embodiment illustrated in FIG. 3, sound processing unit 126 of cochlear implant 100 may be connected directly to fitting system 306 to establish a data communication link 308 between the sound processing unit 126 and fitting system 306. System 306 is thereafter bi-directionally coupled by means of data communication link 308 with sound processing unit 126. It should be appreciated that although sound processing unit 126 and fitting system 306 are connected via a cable in FIG. 3, any communications link now or later developed may be utilized to communicably couple the implant and fitting system.

As an initial matter, audiologist 304 may set up the cochlear implant system 100 and provide the cochlear implant system 100 with an initial set of parameters. This may involve calibrating the cochlear implant 100, as well as determining and setting the threshold and maximum comfortable levels for each stimulation channel of the electrode array 146. An exemplary mechanism for fitting a cochlear implant is provided in U.S. patent application Ser. No. 11/348,309 by James F. Patrick, et al. and entitled "Prosthetic Hearing Implant Fitting Technique," filed Feb. 6, 2006, which is incorporated by reference herein in its entirety. It should be noted however, that this is but one exemplary technique for initially setting up a cochlear implant system, and any technique now or later developed may be used for initially setting up the cochlear implant system. Additionally, during the initial set up, the audiologist may provide a set of default weights to be initially used for each of the stimulation channels.

FIG. 4 is a high-level flow chart illustrating operations that may be performed for adjusting complex stimulation channel weights, in accordance with an embodiment. FIG. 4 will be discussed with reference to the fitting system illustrated in FIG. 3. However, it should be noted that this is exemplary only and provided for explanatory purposes, and the general method of FIG. 4 may be used with other types of systems.

In the discussion below of FIGS. 3 and 4, the exemplary cochlear implant 100 will be assumed to include an electrode array comprising 22 electrodes plus an extra-cochlea electrode and providing 20 tripolar stimulation channels. However, it should be noted that this is exemplary only for explanatory purposes and the method of FIG. 4 may be used with other complex stimulation channels, such as phased-array stimulation channels. A more detailed description of how the process of FIG. 4 may be utilized to adjust the weights for phased-array stimulation channels will be provided below with reference to FIG. 7.

As noted above, these stimulation channels may be tripolar stimulation channels in which current flows from a center electrode (e.g., electrode 2) to its neighboring electrodes (e.g., electrodes 1 and 3) and an extra-cochlea electrode. In initially setting up the cochlear implant 100, audiologist 304 may use the fitting system 306 to assign a set of default weights to each of the electrodes for each stimulation channel, such as, for example, a weight of +1.0 to the center electrode, a weight of −0.3 to each of the neighboring electrodes and a weight of −0.4 to the extra-cochlea electrode, such that each of the neighboring electrodes (e.g., 1 and 3) sink 30% of the current and the extra-cochlea electrode sinks 40% of the current from the center electrode (e.g., 2).

After initially setting-up the cochlear implant system 100 with default weights for the stimulation channels, the process of FIG. 4 may be used to adjust the electrode weights for each stimulation channel to adjust the focus of the stimulation channel. First, fitting system 306 selects a probe channel and a perturbation channel from amongst the plurality of stimulation channels at block 410. In the exemplary 22 electrode array, the first stimulation channel (SC1) is centered at electrode 2 with the neighboring electrodes (1 and 3) and extra-cochlea electrode serving as the sink. This first stimulation channel (SC1) may be chosen as the probe channel. The perturbation channel is selected in this example to be a stimulation channel neighboring the selected probe channel. Thus, in this example, the perturbation channel is selected to be the second stimulation channel (SC2) centered at electrode 3. It should, however, be noted that any stimulation channel may be selected as the initial probe channel in the process of FIG. 4, and the first stimulation channel (SC1) was chosen simply for explanatory purposes. It should also be noted that in embodiments, the audiologist 304, using user interface 314, may select the probe and perturbation channels or override or the channels selected by the fitting system.

Next, fitting system 306 directs the cochlear implant to apply stimulation signals that are applied on the selected probe and perturbation channels and measures their interaction at block 420. Various methods and systems may be used for measuring the interaction between the probe and perturbation channels, and exemplary methods and systems will be discussed in more detail below.

After measuring the interaction between the probe and perturbation channels, the fitting system 306 checks to see if the magnitude of the interaction exceeds a threshold value at block 430. Additionally, in certain situations, the magnitude of the interaction might never fall below the specified threshold. Rather, the measured interaction may alternate between being constructive and destructive as the channel configurations are adjusted, but never drop below the threshold. In such a case, the fitting system 360 may stop the iterative process at block 430 at the point where the magnitude of the interaction is minimized (i.e., the point where the measured interaction alternates between constructive and destructive). In an embodiment, the measured interaction may be determined to be minimized when the magnitude of the measured interaction has not reduced after a pre-determined number of passes through block 430.

If the measured interaction is determined to exceed the threshold and is not determined to be minimized, the fitting system 306 determines whether the interaction between the probe and perturbation channels is constructive or destructive at block 440. As used herein, constructive interaction refers to a perturbation channel that constructively interferes with the probe channel to increase the magnitude of the electric field generated by the probe channel; and, destructive interaction refers to a perturbation channel that destructive interferes with the probe channel to decrease the magnitude of the electric field generated by the probe channel.

If the interaction is constructive, the fitting system 306 adjusts the weights for the probe channel and/or perturbation channel to increase the focus of the probe channel and/or perturbation channel at block 450 and provides the new weights to the cochlear implant 100. However, if the measured interaction is destructive, the fitting system 306 adjusts the weights for the probe channel and/or perturbation channel to decrease the focus of the probe channel and/or perturbation channel at block 460 and provides the new weights to cochlear implant 100. As used herein the term focus refers to the concentration of the electric field produced by the stimulation channel during stimulation of the implanted electrode array. For example, if the focus of the stimulation channel is increased, then the resulting electric field is narrowed. And, decreasing the focus of the stimulation channel refers to widening the resulting electric field.

After the weights are adjusted, the iterative process returns to block 410, where stimulations are applied using the new weights (block 410) and the interaction between the probe and perturbation channels with the updated weights is measured (block 420). This iterative process continues until the measured interaction between the probe and perturbation channels fall below the threshold at block 430. Once the measured interaction is below the threshold, the fitting system 306 next checks, at block 470, if there are additional stimulation channels that should be checked. If so, the process returns to step 410 and new stimulation channels are selected as the probe channel and the perturbation channel. For example, after adjusting the weights for stimulation channel 1 (SC1) as the probe channel, the process may then select stimulation channel 2 (SC2) as the probe channel to adjust the weights of stimulation channel 2 (SC2). As noted above, in embodiments, a neighboring stimulation channel is selected as the perturbation channel. As such, in this second pass through, the fitting system 306 may select either the first (SC1) or third (SC3) stimulation channel as the perturbation channel. The process may then be repeated for each stimulation channel until it is determined at block 470 that all stimulation channels for the cochlear implant 100 have been focused (i.e., had their weights adjusted). After which, the process ends at block 480.

Figure 5A:
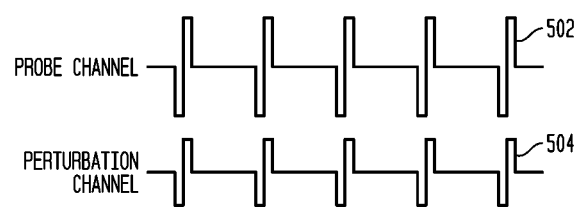
FIG. 5A illustrates exemplary waveforms having the same polarity use in applying stimulation.

As noted above, fitting system 306 at block 420 measures an interaction between the probe and perturbation channels. The following provides a more detailed explanation of an exemplary mechanism that may be employed for measuring the interaction. First, fitting system 306 may direct cochlear implant 100 to apply stimulation on the probe and perturbation channels using an identical waveform shape with the only exception being a difference in overall amplitude between the two waveforms. FIG. 5A illustrates exemplary waveforms for the probe channel 502 and perturbation channel 504 that may be used for application of the stimulation. As illustrated the probe waveform 502 and perturbation waveform 504 have identical shapes and polarities with the only difference being their overall amplitudes. Further, as illustrated, in this example, the waveforms 502 and 504 are biphasic square waves. However, it should be noted that these waveform shapes are exemplary only, and other waveform shapes may be used, such as triangular, sinusoidal, etc. The characteristics of this waveform may be selected by the fitting system 306 and/or audiologist 304.

The amplitude of the perturbation channel stimulation may be set to a level below the perturbation channel's threshold level, referred to herein as a sub-threshold level. As noted above, this threshold level may be determined during set-up of the cochlear implant 100 using fitting system 306. The threshold for the probe channel in the presence of the sub-threshold perturbation channel may then be determined using, for example, a verbal feedback methodology. For example, filtering system 306 may iteratively increase the level of the probe channel in the presence of the sub-threshold perturbation channel until the recipient indicates that they hear the probe channel. The audiologist or clinician 304, using user interface 314, may provide this indication to fitting system 306, or for example, the fitting system 306 may use non-psychophysical measures to measure the interactions (e.g. determine the probe thresholds), such as, for example neural responses telemetry, auditory brainstem response, or other evoked potentials.

Figure 5B:
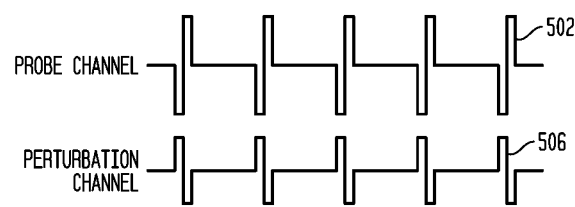
FIG. 5B illustrates exemplary waveforms having opposite polarities for use in applying stimulation.

Next, the polarity of the perturbation channel may be reversed and stimulation simultaneously applied on probe channel and perturbation channels. FIG. 5B illustrates exemplary waveforms for the probe channel 502 and perturbation channel 506. As illustrated, the probe channel waveform 502 is the same as in FIG. 5A, and that the perturbation channel waveform 506 is identical to perturbation channel waveform 504 but has an opposite polarity. The threshold of the probe channel in the presence of the perturbation channel with the opposite polarity is then determined with the level of the perturbation channel set to the same previously used sub-threshold level.

After determining the two probe threshold values (one with a perturbation channel with the same polarity and one with a perturbation channel with the opposite polarity), an interaction index (II) may be computed. This II may use the following formula:

$$II(\text{probe, pert}) = \frac{probeThreshold(\text{opposite}) - probeThreshold(\text{same})}{2 * perturbationChannelLevel},$$

wherein II(probe, pert) is the interaction index of the probe and perturbation channels, probeThreshold(opposite) is the threshold of the probe channel measurement with the perturbation channel having the opposite polarity as the probe channel, probeThreshold(same) is the threshold of the probe channel measurement with the perturbation channel having an same polarity as the probe channel and perturbationChannelLevel is the sub-threshold level of the perturbation channel used in determining the probe threshold levels. In an embodiment, the probe channel thresholds and perturbation channel levels used in this formula are in linear current units.

The fitting system 306 may then, at block 430, compare the magnitude of the computed interaction index (II) against the threshold to determine if the magnitude of the interaction index (II) falls below the threshold or not. If not, this indicates that the interaction between the probe and perturbation channels is significant. And, if so, the interaction is determined to be insignificant.

In addition to determining whether the interaction is significant or not, the fitting system 306 may also use this computed interaction index (II) in block 440 to determine whether the interaction is constructive or destructive. For example, in this example, if the interaction index (II) is positive (i.e., >0), the interaction may be determined to be constructive, and if the interaction index (II) is negative (i.e., <0) the interaction may be determined to be destructive at block 440.

FIGS. 6A-6D illustrate exemplary electric fields generated by exemplary probe and perturbation channels and will be used to illustrate constructive and destructive interactions between the channels. FIG. 6A illustrates a probe channel electric field 602 and a perturbation channel electric field 604 where the perturbation channel has the same polarity as the probe channel. FIG. 6B illustrates the combined electric field 614 resulting from the combined the probe channel electric field 602 and perturbation channel electric field 604 where the polarities are the same. FIG. 6C illustrates the probe channel electric field 602 and a perturbation channel electric field 606 where the perturbation channel has the opposite polarity as the probe channel. FIG. 6D illustrates the combined electric field 616 resulting from the combined the probe channel electric field 602 and perturbation channel electric field 606 where the polarities are opposite. In FIGS. 6A-D, the horizontal axis is a location along the electrode array and the vertical axis is potential of the electric field. Further, the dotted line 601 is included merely to add perspective to aid the reader in seeing the different levels of the resulting electric fields.

Constructive interference occurs when the electric field 614 resulting from common polarities is greater than the resulting electric field resulting 616 from opposite polarities, and destructive interference occurs when the electric field 614 resulting from common polarities is less than the resulting electric field resulting 616 from opposite polarities. Referring to the above-discussed Interaction Index (II), constructive interference may be recognized by when the determined probe threshold for common polarities is less than the probe threshold for opposite polarities between the probe and perturbation channels, and destructive interference when the opposite occurs.

As noted above, in blocks 450 and 460 the focus of the probe channel and/or perturbation channel may be increased or decreased by respectively adjusting the weights for the probe channel and/or perturbation channel. In a cochlear implant 100 using tripolar stimulation with an extracochlear electrode, the focus may be increased, for example, by fitting system 306 increasing the magnitudes of the weights of one or both of the neighboring electrodes (e.g., electrodes 1 and/or 3) and decreasing the magnitude of the weight of the extra-cochlear electrode. For example, initially, the neighboring electrodes may be assigned a weight of −0.3 and the extra-cochlea electrode assigned a weight of −0.4. It should be noted that in this example, the weight of the center electrode is always set to +1.0 for tripolar stimulation and that the summed value of all the weights in a given channel is equal to 0.

In adjusting the focus, the fitting system 306 may increase the focus by, for example, increasing the magnitudes of the weights of one or both of the neighboring electrodes in steps of 0.05 and decreasing the magnitude of the weight of the extra-cochlea electrode in steps of 0.5 or 0.1 respectively. It should be noted these values are exemplary only. Similarly, the focus of the probe channel and/or perturbation channel may be decreased by decreasing the magnitudes of the weights of the neighboring electrodes and increasing the magnitude of the weight of the extra-cochlear electrode. It should be noted that this is but one example of how weights may be adjusted and other mechanisms may be used. For example, a scalar may be used to multiply or divide the weights in adjusting the weights. Or, for example, a mechanism may be used where the step size is adjusted such that a large step size is used initially and then reduced depending on certain conditions, such as if the interaction goes from constructive to destructive or visa versa.

As noted above, the method and systems of FIGS. 3-4 may be used for adjusting the weights for other types of complex channels besides tripolar channels, such as, for example, phased-array stimulation channels. The following provides an exemplary description of methods and systems for adjusting the weights for phased-array stimulation channels. As discussed in more detail in the van den Honert references, the default weights for phased array stimulation channels may be determined by computing the transimpedance matrix for the cochlear implant 100 and then inverting the transimpedance matrix to provide the weights for the stimulation channels.

Figure 7:
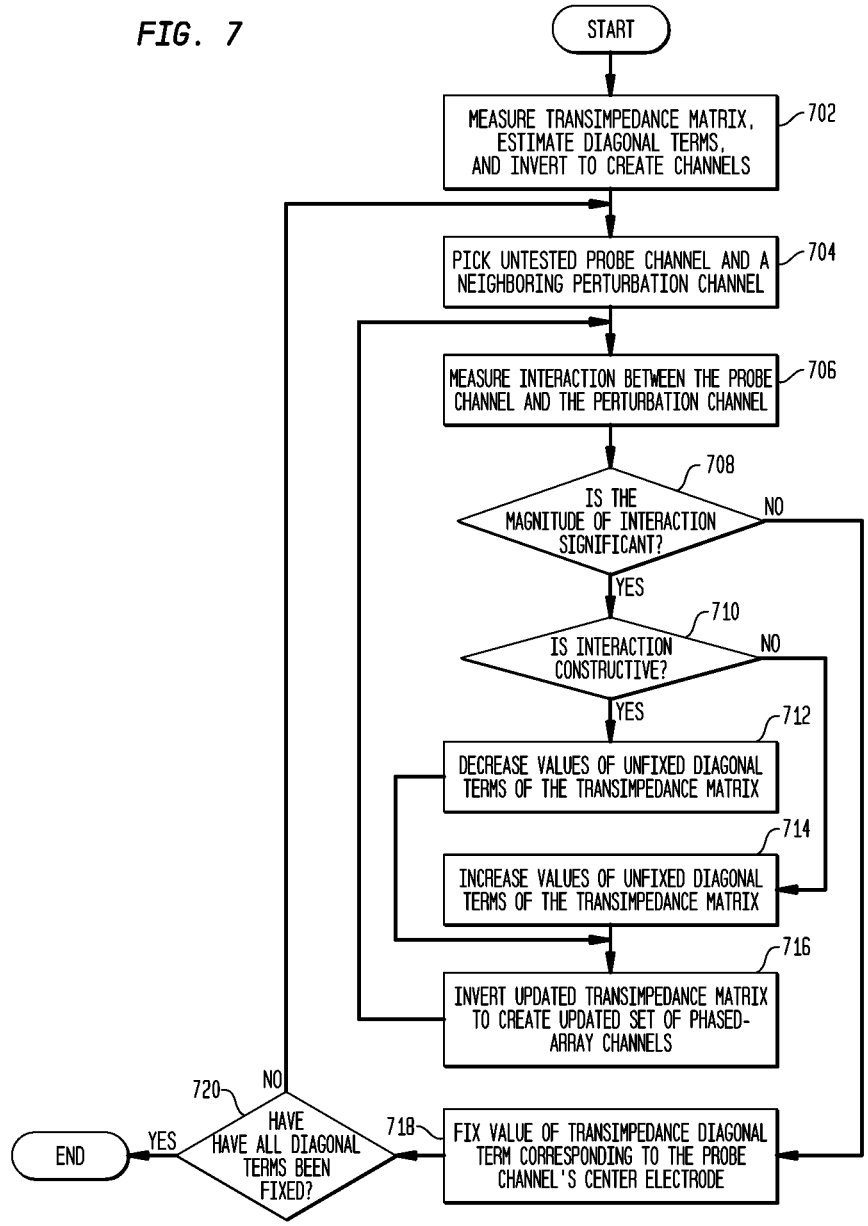
FIG. 7 provides a flow chart for adjusting the weights for phased-array stimulation channels, in accordance with an embodiment.

FIG. 7 provides a flow chart for how the general method FIG. 4 may be used for adjusting the weights for phased-array stimulation channels, in accordance with an embodiment. FIG. 7 will be discussed in reference to the fitting arrangement system 300 discussed above. However, it should be noted that other systems may be used.

Figure 8:
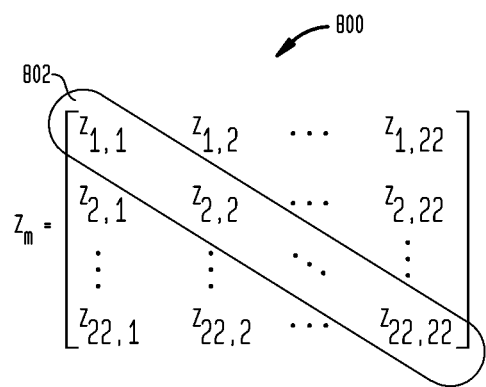
FIG. 8 illustrates an exemplary transimpedance matrix, in accordance with embodiments.

Initially, at block 702, an initial transimpedance matrix is obtained. This transimpedance matrix may be obtained, such as, for example, as discussed in the van den Honert references. FIG. 8 illustrates an exemplary transimpedance matrix, $Z_m$, in accordance with embodiments. As illustrated, transimpedance matrix, $Z_m$, 800 comprises 22 columns and 22 rows. Each column and row corresponds to a particular electrode of an exemplary electrode array comprising 22 electrodes, where a row corresponds to the electrode on which stimulation is applied in measuring the transimpedance matrix. And, a column corresponds to the electrode on which the applied stimulation is measured in obtaining the transimpedance matrix. As discussed in the van den Honert references, all values, except the diagonal, of the transimpedance matrix may be empirically measured by stimulating each electrode with a known current, one at a time. Then, the resulting voltage at each non-stimulated electrode is measured. Because voltage observed on the stimulating electrode includes parts from the bulk resistance and tissue impedance, the diagonal of the transimpendence matrix is not determined in this manner. Rather, according to the van den Honert references, the values along the diagonal 802 of transimpendence matrix 800 may be estimated by linear extrapolation of the values surrounding the diagonal values. Methods and systems for obtaining the transimpedance matrix and estimating the diagonal values 802 are provided in the above-incorporated by reference van den Honert references, and are not discussed further herein. Although transimpedance matrix, $Z_m$, 800 comprises 22 columns and 22 rows, it should be noted that this is exemplary only, and in other embodiments electrodes arrays comprising a different number of electrodes other than 22 may be used.

Once the transimpedance matrix is obtained with the estimated diagonal values, the fitting system 306 then inverts the transimpendence matrix to obtain an initial set of weights for the phased-array channels. Particularly each column of the inverted transimpedance matrix (also known as the transadmittance matrix) comprises a set of numerical weights (transadmittance values) defining the current contribution from each electrode for producing a non-zero intrascalar voltage at a single discrete stimulation region. As such, each such vector of weights defines a phased-array stimulation channel.

The fitting system 306, at block 704, selects one of the stimulation channels as a probe channel and a neighboring channel as the perturbation channel. Interactions are then measured between the selected probe and perturbation channels at block 706. This may be accomplished in the same manner as discussed above with reference to block 420 of FIG. 4. Particularly, in an embodiment, the interaction may be measured by determining the threshold of the probe channel while simultaneously stimulating the perturbation channel at a fixed sub-threshold level. The shape of the current waveforms delivered to each channel for application of the stimulation may be identical, except for a scalar multiplier, such as the waveforms illustrated in FIGS. 5A-B.

The threshold of the probe channel may be measured twice, once with the perturbation channel having the same polarity as the probe, and once with the perturbation channel having the opposite polarity of the probe channel. The level of the perturbation channel is fixed for both threshold determinations. The above-discussed interaction index (II) may then be computed:

$$II(\text{probe, pert}) = \frac{probeThreshold(\text{opposite}) - probeThreshold(\text{same})}{2 * perturbationChannelLevel},$$

The fitting system 306 may then determine, at block 708, whether the magnitude of the computed Interference Index (II) exceeds a threshold value. An exemplary threshold would be an II of 0.05, though other values other than 0.05 may be used depending on the accuracy of the interaction index measures. If threshold is exceeded, the fitting system may then determine, at block 710, whether the interactions are constructive or destructive. As noted above, the fitting system 306 may determine whether the interaction is constructive or destructive by checking whether the Interference Index (II) is positive (i.e., constructive interference) or negative (i.e., destructive interference).

If the interactions are significant and constructive, the fitting system 306 may adjust the transimpedance matrix to increase the focus of the stimulation channels at block 712. This may be accomplished by decreasing all unfixed diagonal terms of the transimpedance matrix. The value of the diagonal term corresponding to a particular stimulation channel's electrode center, in embodiments, has the most significant impact on the focus of that stimulation channel. Accordingly, in other embodiments, the fitting system 306 my only decrease the value of the diagonal term corresponding to the probe channel's electrode center, or a subset of the values surrounding this term, as opposed to decreasing the values of all unfixed terms.

If the interactions are significant and destructive, the fitting system 306 may, at block 714, increase the values of the unfixed diagonal terms of the transimpedance matrix to decrease the focus of the stimulation channels. Or, for example, fitting system 306 may only increase the value of the term corresponding to the probe channel's electrode center or a subset of the values surrounding this term. New channel weights are then computed from the updated transimpedance matrix, at block 716, and the iterative procedure continues by measuring interactions between probe and perturbation channels using the new weights.

If, at block 708, the magnitude of the Interaction Index (II) is below the threshold, then, the iterative procedure is stopped for this particular probe channel and the fitting system 306 sets the final value of the diagonal term of the transimpedance matrix corresponding to the electrode center of the probe channel as fixed. The fitting system 306 may set a diagonal term as fixed by simply storing an indication in a memory or other storage device that identifies that the particular diagonal term is fixed. The fitting system 306 then, at block 720, determines whether all diagonal terms have been fixed. If not, the process returns to Step 704 where the optimization procedure is repeated for a different stimulation channel selected as the probe channel. This process then repeats until all channels have been tested as the probe channel, and all diagonal values have been fixed.

Referring back to blocks 712 and 714, the fitting system 306 may adjust the diagonal term, such as the value corresponding to the probe channel's electrode center and/or the unfixed terms, in a variety manners. For example, in an embodiment, a variable, referred to herein as a phased array compensation factor (PACF), may be used to determine a multiplication factor (MF). And, the diagonal term(s) may be adjusted by multiplying the diagonal term(s) by this multiplication factor (MF). In an embodiment, the relationship between the PACF and MF may be defined as follows:

$$PACF=1-(1/MF), \text{ or}$$

$$MF=1/(1-PACF), \text{ where}$$

$$0 \leq PACF \leq 1$$

In adjusting the diagonal terms, the fitting system 306 may initially set the PACF to a particular value, such as, PACF=0.0 and then compute the corresponding MF (i.e., MF=1). Then, the fitting system 306 may multiply the diagonal terms (e.g., the unfixed terms, the diagonal term corresponding to the probe electrode center, etc.) by MF, and compute the II with the new diagonal terms. The PACF may then be increased by a particular step size (e.g., +0.2) with each subsequent iteration. That, in the next iteration PACF=0.2 and, thus MF=1.25. This step size (e.g., 0.2) may be used until the opposite condition occurs (i.e., the value of the Interaction Index (II) goes from negative to positive or visa versa). The step size may then be halved and its sign reversed (e.g., −0.1) and the process repeated. In other words, if increasing the PACF, an initial step size (e.g., +0.2), may be used until the Interaction Index (II) is positive (constructive), then the step size may be reduce (e.g., halved) and its sign reversed (i.e., reduced to −0.1) and used to reduce the value until the II becomes negative, and then reduced (e.g., halved) again (i.e. reduced to +0.05), and so on until the II value falls below the threshold. It should be noted that this is but one example of how the values of the diagonal terms may be adjusted and other methods can be used without departing from the invention as claimed.

For example, in an alternative embodiment, rather than adjusting one stimulation channel at a time and fixing the diagonal values at the end of each iteration, the system may not fix any terms until finalized and instead adjust all or some of the diagonal values on each iteration. It should, however, be understood that these are but some exemplary methods that may be used for adjusting the weights to minimize interactions and other methods may be used without departing from the invention.

At the end of the iterative process, when interactions between all possible probe channels and the corresponding perturbation channels (i.e., a channel neighboring the probe channel) are minimized, the fitting system 306 may use the final values to generate the electrode weights for stimulation channels and then provide these weights to the cochlear implant 100. The cochlear implant 100 may then store and use these weights in the sound processing unit 126 and/or the stimulator unit 120. In another embodiment of the invention, the iterative optimization process for each probe/perturbation channel pair can be terminated early by estimating channel configurations at the point of insignificant interaction. For example, the estimation of channel configurations may be done by interpolating between iterations of optimization that respectively show constructive and destructive interactions. In another embodiment of the invention, the iterative optimization process for each probe/perturbation channel pair may never reach a point of insignificant interaction and the iterative procedure may be stopped at a minimum magnitude or estimated minimum magnitude of the interaction.

This embodiment, therefore, provides customized complex-channel configurations for an individual ear, narrow neural excitation patterns and increased number of independent channels. The embodiment may also raise the upper limit on stimulation rates because multiple channels can be stimulated simultaneously, and also provides for better spectral resolution and reduced channel interactions.

It should be understood that the method and systems discussed above for measuring the channel interactions are merely one mechanism that may be employed for measuring the channel interactions. For example, in other embodiments, the fitting system may measure the channel interactions by simultaneously applying a stimulation signal on a probe and perturbation channel with the same polarities and comparing the determined probe threshold with the probe threshold determined during the set-up process, which was determined without the presence of any perturbation channel. This difference between the probe threshold in the presence of the perturbation channel and in the absence of the perturbation channel can be compared against a threshold. If the difference is greater than the threshold the focus of the probe channel may then be accordingly modified. Similarly, in another embodiment, stimulation signals may be applied on both the probe and perturbation channels, where the probe threshold is first determined with a perturbation channel of the same polarity and then with a perturbation channel of the opposite polarity. But, in this example, rather than setting the perturbation channel to a fixed subthreshold level, the probe and perturbation channels may be set and adjusted to the same levels, and the probe thresholds for each polarity determined in this manner. Then, the difference in probe thresholds for each polarity may be compared against a threshold value to determine whether or not the interactions between the channels are significant or not.

In yet another embodiment, the fitting system may measure the interactions by using a particular loudness as opposed to determining thresholds. For example, the level of the probe channel for each polarity of the perturbation channel may be increased until the recipient indicates that the loudness of the probe channel matches a fixed loudness level. These levels may then be used to measure the channel actions, and the weights adjusted based on this measurement, such as was discussed above. In yet another example, the fitting system 306 may be used to apply two instances of a supra-threshold probe channel having the same level in the presence of a subthreshold perturbation channel with the same polarity in the first instance, and with the opposite polarity in the second instance. The recipient may then determine which of these stimulations sounds louder (i.e. whether the sound is louder when the probe and perturbation channels have the same polarity or opposite polarities). If the recipient perceives a noticeable difference, the channel interactions may be determined to be significant and the weights accordingly adjusted. In yet another example, the fitting system need not apply the probe and perturbation channels simultaneously, but instead may apply the two stimulation signals one right after the other or with a small time difference between them. As such, there are numerous other mechanisms for determining the channel interactions that may be used without departing from the invention as claimed.

Figure 9:
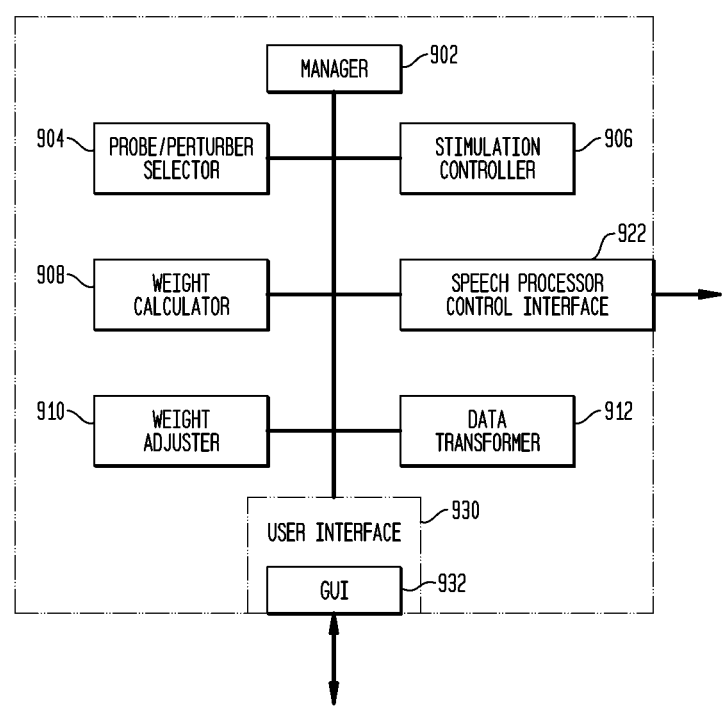
FIG. 9 is a high-level functional block diagram of hearing implant fitting system in accordance with an embodiment.

FIG. 9 is a high-level functional block diagram of hearing implant fitting system 306 in accordance with an embodiment of the present invention. The primary components and operative aspects of fitting system 206 are shown in block diagram form for ease of description and it should be understood that these blocks may be split apart or combined in numerous other ways. In the exemplary embodiment shown in FIG. 9, the components are shown as being coupled by a communications bus. However, it is to be understood that the components of fitting system 306 may be connected in any manner suitable for the particular application.

As illustrated, fitting system 306 comprises a manager 902, probe/perturber select 904 stimulation controller 906, weight calculator 908, weight adjuster 910, data transformer 912, speech processor control interface 922, and user interface 930. Manager 902 performs general operations and controls the other components shown in FIG. 9. Speech processor control interface 922 may provide an interface for connecting fitting system 306 to the speech processor of cochlear implant 100 via data communication link 308. Probe/Pertuber selector 904 may be responsible for selecting, at the direction of manager 902, the stimulation channels to function as the probe channel and perturbation channel. Stimulation controller 906 controls the application of the stimulation on the selected probe and perturber channels. For example, the stimulation controller 906 may be responsible for selecting the waveform to be applied, its amplitude, polarity, etc. and sending information to cause the cochlear implant to apply the stimulations. For example, in embodiments, the stimulation controller 906 may generate the selected waveforms and send the waveforms to the cochlear implant, via speech processor control interface 922, for application of the stimulation on the selected probe and perturbation channels. Or, for example, stimulation controller may send instructions to the speech processing unit 126 to generate the selected signals and apply the stimulation.

User interface 930 may include any interface which is used by audiologist/clinician 304 to communicate with fitting implant system 306 via user interface 314. The audiologist/clinician 304 can provide input using any one or combination of known methods, including a computer keyboard, mouse, voice-responsive software, touch-screen, retinal control, joystick, and any other data entry or data presentation formats now or later developed.

In the embodiment illustrated in FIG. 9, user interface 930 may include a graphical user interface (GUI) 408 which is displayed by user interface 314, above. As noted, user interface 406 may be used to provide and receive acoustic-based data; such as, for example, the selected probe and perturbation channels as well as their levels, weights, etc. via user interface 314. In addition, the audiologist/clinician 304 may use a graphical user interface (GUI) 408 to enter information regarding the results of the stimulations, such as whether or not the recipient hears the probe channel in the presence of the subthreshold perturbation channel. Additionally, the GUI 408 may be used while setting up the cochlear implant, such as, for example, to input/receive information when determining the initial threshold and maximum comfort levels for each electrode of the electrode array.

As illustrated in FIG. 9, fitting system 306 may also comprise a weight calculator 908 that determine the weights for each stimulation channel. For example, in a cochlear implant system employing phased-array stimulation channels, weight calculator 908 may be responsible for inverting the transimpedance matrix and determining the weights for each channel. Fitting system 306 may also comprise a weight adjuster 910 configured to adjust the weights of each stimulation channel. For example, weight adjuster 910 may calculate the Interaction Index (II) based on the received probe channel thresholds for each polarization, determine whether the weights should be adjusted, and if so, the step-size for the adjustment, as well as making the determined adjustments. In a phased-array stimulation system, weight adjuster 910 may adjust the diagonal values of the transimpedance matrix in making the adjustments, and then provide the modified transimpedance matrix to the weight calculator 908, which calculates the new weights for the channels. For a tripolar stimulation system, weight adjuster 910 may directly adjust the weights of the stimulation channels.

In the exemplary embodiment illustrated in FIG. 9, fitting system 206 may also comprise an acoustic-cochlear implant (CI) data transformer 912 that transforms the determined weights and other data (e.g., threshold and maximum comfort level data) to implant-based map data 322 for the cochlear implant 100. This map data 322 may be in any form suitable for the implemented cochlear implant 100. This map data 322 generated by data transformer 916 may then be provided to the sound processing unit 126 via speech processor control interface 922.

The subject matter described herein may be embodied in various systems, apparatus, methods, and/or articles depending on the desired configuration. Particularly, various implementations of the subject matter described, such as the embodiment of FIG. 9, components may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device These computer programs (also known as programs, software, software applications, applications, components, or code) include machine instructions for a programmable processor, and may be implemented in a high-level procedural and/or object-oriented programming language, and/or in assembly/machine language. As used herein, the term "machine-readable medium" refers to any computer program product, computer-readable medium, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. Similarly, systems are also described herein that may include a processor and a memory coupled to the processor. The memory may include one or more programs that cause the processor to perform one or more of the operations described herein.

All documents, patents, journal articles and other materials cited in the present application are hereby incorporated by reference.

Embodiments of the present invention have been described with reference to several aspects of the present invention. It would be appreciated that embodiments described in the context of one aspect may be used in other aspects without departing from the scope of the present invention.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart there from.

The foregoing description has been directed to specific embodiments of this invention. It will be apparent; however, that other variations and modifications may be made to the described embodiments, with the attainment of some or all of their advantages. Therefore, it is the object of the appended claims to cover all such variations and modifications as come within the true spirit and scope of the invention

What is claimed is:

1. A method for adjusting weights of a stimulating device comprising a plurality of stimulation channels, wherein each stimulation channel comprises a plurality of electrodes each having a corresponding weight, the method comprising:
    selecting a probe channel from amongst the plurality of stimulation channels;
    selecting at least one perturbation channel from amongst the plurality of stimulation channels;
    applying stimulation via the probe channel using the plurality of electrodes and their corresponding weights;
    applying stimulation via the at least one perturbation channel;
    measuring an interaction between the stimulation via the probe channel and the stimulation via the at least one perturbation channel; and
    adjusting one or more weights for at least one electrode of at least one of the stimulation channels based on the measured interaction between the stimulation via the probe channel and the stimulation via the at least one perturbation channel.

2. The method of claim 1, further comprising:
    determining whether the measured interaction exceeds a threshold; and
    wherein adjusting the one or more weights comprises:
        adjusting the one or more weights when the measured interaction is determined to exceed the threshold.

3. The method of claim 2, further comprising:
    determining whether the measured interaction is a constructive or destructive interaction.

4. The method of claim 3, wherein the adjusting comprises adjusting the weights to increase the focus if the measured interaction is determined to be constructive; and
    wherein the adjusting comprises adjusting the weights to decrease the focus if the measured interaction is determined to be destructive.

5. The method of claim 2, further comprising:
    repeating, at the probe channel and at the at least one perturbation channel, the applying, measuring, determining and adjusting until the measured interaction is determined to be below the threshold or the measured interaction is determined to be minimized.

6. The method of claim 5 further comprising:
    repeating the selecting a probe channel, selecting at least one perturbation channel, and repeating for each channel of the plurality of channels as the probe channel.

7. The method of claim 2, wherein each of the probe channel and the at least one perturbation channel have a polarity,
    wherein applying a stimulation signal via the at least one perturbation channel comprises
        applying a stimulation signal wherein the probe channel and the at least one perturbation channel have the same polarity, and
        applying a stimulation signal wherein the probe channel and the at least one perturbation channel have the opposite polarity; and
    wherein the measuring comprises:
        measuring the interaction between the at least one perturbation channel and the probe channel having the same polarity, and
        measuring the interaction between the at least one perturbation channel and the probe channel having opposite polarity.

8. The method of claim 1, wherein the weights of the stimulation channels are determined using a transimpedance matrix; and
    wherein the adjusting one or more weights comprises:
        adjusting one or more values of the transimpedance matrix.

9. The method of claim 8, wherein adjusting one or more values of the transimpedance matrix comprises:
    adjusting one or more diagonal terms of the transimpedance matrix.

10. The method of claim 9, wherein the adjusting one or more diagonal terms of the transimpedance matrix comprises:
    decreasing one or more values of the diagonal if the interaction is determined to be constructive; and
    increasing one or more values of the diagonal if the interaction is determined to be destructive.

11. The method of claim 1, wherein:
    the action of applying stimulation via the at least one probe channel and the action of applying stimulation via the at least one perturbation channel are executed simultaneously.

12. An apparatus for use in adjusting weights of a stimulating device comprising a plurality of stimulation channels, the apparatus comprising:
    a selector configured to select a probe channel from amongst the plurality of stimulation channels, wherein the probe channel comprises a plurality of electrodes each associated with a corresponding weight, and to select at least one perturbation channel from amongst the plurality of stimulation channels;
    a stimulation controller configured to transmit information for applying stimulation via the probe channel using the plurality of electrodes and their corresponding weights, and stimulation via the at least one perturbation channel; and
    a weight adjuster configured to adjust one or more weights for at least one electrode of at least one of the stimulation channels based on an interaction between the stimulation via the probe channel and the stimulation via the at least one perturbation channel.

13. The apparatus of claim 12, wherein the weight adjuster is further configured to measure the interaction between the stimulation from the probe channel and the stimulation of the at least one perturbation channel, determine whether the measured interaction exceeds a threshold, and adjust the one or more weights if the measured interaction is determined to exceed the threshold.

14. The apparatus of claim 13, wherein weight adjuster is further configured to determine whether the measured interaction is a constructive or destructive interaction.

15. The apparatus of claim 14, wherein the weight adjuster is further configured to adjust the weights to increase the focus if the measured interaction is determined to be constructive; and
adjust the weights to decrease the focus if the measured interaction is determined to be destructive.

16. The apparatus of claim 13, wherein each of the probe channel and the at least one perturbation channel have a polarity,
wherein the stimulation controller is further configured to transmit information for applying stimulation regarding applying a stimulation signal wherein the probe channel and the at least one perturbation channel have the same polarity, and applying a stimulation signal wherein the probe channel and the at least one perturbation channel have the opposite polarity; and
wherein the weight adjuster is further configured to measure the interaction between the at least one perturbation channel and the probe channel having the same polarity, and measure the interaction between the at least one perturbation channel and the probe channel having opposite polarity.

17. The apparatus of claim 12, further comprising:
a weight calculator configured to determine the weights of the stimulation channels using a transimpedance matrix; and
wherein the weight adjuster is further configured to adjust one or more weights by adjusting one or more values of the transimpedance matrix.

18. The apparatus of claim 17, wherein the weight adjuster is further configured to adjust one or more diagonal terms of the transimpedance matrix.

19. The apparatus of claim 18, wherein the weight adjuster is further configured to decrease one or more values of the diagonal if the interaction is determined to be constructive; and increase one or more values of the diagonal if the interaction is determined to be destructive.

20. The apparatus of claim 12, wherein the apparatus is configured such that the stimulation applied via the probe channel and the stimulation applied via the at least one perturbation channel are applied simultaneously.

21. A computer program embodied on a non-transitory computer readable medium, the computer program comprising program code for controlling a processor to execute a method for adjusting weights of a stimulating device comprising a plurality of stimulation channels, wherein each stimulation channel comprises a plurality of electrodes each having a corresponding weight, the method comprising:
selecting a probe channel from amongst the plurality of stimulation channels;
selecting at least one perturbation channel from amongst the plurality of stimulation channels;
applying stimulation via the probe channel using the plurality of electrodes and their corresponding weights;
applying stimulation via the at least one perturbation channel;
measuring an interaction between the stimulation via the probe channel and the stimulation via the at least one perturbation channel; and
adjusting one or more weights for at least one electrode of at least one of the stimulation channels based on the measured interaction between the stimulation via the probe channel and the stimulation via the at least one perturbation channel.

22. The computer program of claim 21, wherein the method comprises:
applying stimulation via the at least one probe channel and applying stimulation via the at least one perturbation channel simultaneously.

23. An apparatus for adjusting weights of a stimulating device comprising a plurality of stimulation channels, wherein each stimulation channel comprises a plurality of electrodes each having a corresponding weight, the apparatus comprising:
means for selecting a probe channel from amongst the plurality of stimulation channels;
means for selecting at least one perturbation channel from amongst the plurality of stimulation channels;
means for applying stimulation via the probe channel using the plurality of electrodes and their corresponding weights;
means for applying stimulation via the at least one perturbation channel;
means for measuring an interaction between the stimulation via the probe channel and the stimulation via the at least one perturbation channel;
means for adjusting one or more weights for at least one electrode of at least one of the stimulation channels based on the measured interaction between the stimulation via the probe channel and the stimulation via the at least one perturbation channel.

24. The apparatus of claim 23, wherein the apparatus is configured such that the stimulation applied via the probe channel and the stimulation applied via the at least one perturbation channel are applied simultaneously.

* * * * *

UNITED STATES PATENT AND TRADEMARK OFFICE
CERTIFICATE OF CORRECTION

PATENT NO. : 8,954,158 B2
APPLICATION NO. : 12/366510
DATED : February 10, 2015
INVENTOR(S) : Zachary M. Smith It is certified that error appears in the above-identified patent and that said Letters Patent is hereby corrected as shown below:

In the Claims

Column 20, Line 40, after "perturbation channel" insert the word --and--

Signed and Sealed this
Fifth Day of July, 2016

Michelle K. Lee
*Director of the United States Patent and Trademark Office*